US012011117B2

(12) United States Patent
Boras et al.

(10) Patent No.: US 12,011,117 B2
(45) Date of Patent: Jun. 18, 2024

(54) CHOPPING BOARD

(71) Applicant: Aurora Life Science GmbH, Darmstadt (DE)

(72) Inventors: Philo Boras, Darmstadt (DE); Jonathan Oberthür, Darmstadt (DE)

(73) Assignee: Aurora Life Science GmbH, Darmstadt (DE)

( * ) Notice: Subject to any disclaimer, the term of this patent is extended or adjusted under 35 U.S.C. 154(b) by 423 days.

(21) Appl. No.: 17/600,869

(22) PCT Filed: Mar. 30, 2020

(86) PCT No.: PCT/EP2020/058908
§ 371 (c)(1),
(2) Date: Oct. 1, 2021

(87) PCT Pub. No.: WO2020/201192
PCT Pub. Date: Oct. 8, 2020

(65) Prior Publication Data
US 2022/0167800 A1    Jun. 2, 2022

(30) Foreign Application Priority Data
Apr. 3, 2019  (DE) ...................... 10 2019 108 711.2

(51) Int. Cl.
*A47J 47/00* (2006.01)
*A47J 47/16* (2006.01)
(Continued)

(52) U.S. Cl.
CPC ............ *A47J 47/005* (2013.01); *A47J 47/16* (2013.01); *G01G 19/52* (2013.01); *G01N 21/45* (2013.01); *G01N 33/02* (2013.01)

(58) Field of Classification Search
CPC ........ A47J 47/005; A47J 47/16; G01N 21/45; G01N 33/02; G01G 19/52
See application file for complete search history.

(56) References Cited

U.S. PATENT DOCUMENTS 6,359,239 B1 * 3/2002 Missler ................. G01G 21/22
708/133
10,101,521 B1    10/2018 Burgio, Jr.
(Continued)

FOREIGN PATENT DOCUMENTS

DE    102015110096 A1    12/2016
EP         2548469 B1     1/2013
(Continued)

*Primary Examiner* — Seahee Hong

(57) ABSTRACT

A chopping board for foodstuffs has a base and an upper part which can be arranged detachably on the base. A cutting surface on which foodstuff to be chopped can be arranged and cut is formed on an upper-part upper side. The upper part has connecting elements, by which the upper part is located on the base. The base of the chopping board has at least one bearing surface by which the chopping board sits on a supporting surface. The upper part has an optical element, by which electromagnetic radiation emitted and/or reflected by the cut foodstuff, in particular near-IR light, is propagated. At least one radiation sensor for detecting electromagnetic radiation, more particularly an interferometer, is arranged in a sensor area of the base assigned to the optical element, by which sensor the electromagnetic radiation is detected, so that characteristics of the foodstuff to be chopped can be determined.

15 Claims, 2 Drawing Sheets

(51) Int. Cl.
*G01G 19/52* (2006.01)
*G01N 21/45* (2006.01)
*G01N 33/02* (2006.01)

(56) References Cited

U.S. PATENT DOCUMENTS

| | | | |
|---|---|---|---|
| 2007/0001359 A1* | 1/2007 | Pearl | A47J 47/005 269/289 R |
| 2015/0076974 A1 | 3/2015 | Schreiter | |
| 2016/0374516 A1* | 12/2016 | Lammel | G01G 19/56 269/11 |
| 2018/0263425 A1 | 9/2018 | Dickie et al. | |
| 2020/0288917 A1* | 9/2020 | Frielinghaus | A47J 47/005 |

FOREIGN PATENT DOCUMENTS

| | | |
|---|---|---|
| EP | 2840932 | 10/2013 |
| WO | 2018202375 A1 | 11/2018 |

\* cited by examiner

CHOPPING BOARD

TECHNICAL FIELD

The disclosure relates to a chopping board for foodstuffs.

BACKGROUND

In both the private and the professional sphere, cooks are nowadays faced with a multiplicity of utensils. With the increasing number of cooking utensils available, however, the demands made in terms of organizing the work and the workspace in a kitchen increase. One approach to solving this problem is the chopping board described in EP 2840932 B1. The chopping board disclosed therein is a kitchen worktop which has holders for standardized kitchen containers which make it possible for options for receiving uncut ingredients, cut ingredients and for waste to be provided around a worktop formed by the board. This improves the organization of work when handling foodstuff to be chopped. What is disadvantageous about the disclosed chopping board, however, is that it is still necessary to weigh the individual ingredients, or foodstuffs to be handled, by means of separate scales.

One further aspect which in recent years has become more and more important in the modern restaurant field but also when cooking at home is the quality of the foodstuffs handled. "Quality" in this context means firstly the freshness of foodstuffs, for example fish, meat, fungi or the like, and also the degree of ripeness, for example of fruit. The foodstuff quality can be determined in particular by means of optical measuring methods. What is disadvantageous about the known measuring methods is that they have to be carried out by means of separate equipment, the use of which disrupts the workflows in a kitchen, which is why they are frequently not used.

SUMMARY

It is an object of the present invention to provide a chopping board by means of which determination of parameters of foodstuffs to be handled is facilitated.

The object is achieved by a chopping board for foodstuffs, having a base and at least one upper part which can be arranged detachably on the base, wherein a cutting surface on which foodstuff to be chopped can be arranged and cut is formed on an upper-part upper side facing away from the base when the upper part is arranged as intended on the base, wherein the upper part comprises fasteners, by means of which the upper part is located on the base, on an upper-part lower side opposite the cutting surface and facing the base, wherein the base of the chopping board comprises at least one bearing surface on a base lower side facing away from the upper part, by means of which bearing surface the chopping board sits on a supporting surface. The upper part comprises at least one optical element, by means of which electromagnetic radiation emitted and/or reflected by the foodstuff to be chopped, in particular electromagnetic radiation in the near-infrared range, can be propagated through the upper part, wherein at least one radiation sensor for detecting electromagnetic radiation, more particularly an interferometer, is arranged in a sensor area of the base assigned to the optical element, by means of which sensor the electromagnetic radiation can be detected, so that characteristics of the foodstuff to be chopped can be determined. Such a configuration of the chopping board according to the invention makes it possible for the foodstuff to be chopped to be held in front of the sensor in a simple manner during handling, and thus for determination of the quality of the foodstuff to be chopped to be able to be carried out.

"Optical element" within the meaning of the inventive concept means in particular lenses, glass discs, magnifying glasses, optical waveguides, camera arrangements or the like. Provision is made for different optical elements to be used depending on what type of electromagnetic radiation is used to investigate the foodstuff to be chopped. Furthermore, it is also possible and provided according to the invention that a plurality of optical elements can be provided with one or more sensors.

It is also possible and provided that the optical element may have a filter, or merely be transparent to a particular spectrum of electromagnetic radiation. For example, plastics materials are known which are transparent merely to infrared radiation. Furthermore, the optical element may also have a polarization filter.

Provision is made that the sensor may be in particular an interferometer, a photosensor, a Geiger counter or the like. Use of a Geiger counter may be useful in particular if game or fungi are being handled, as these are occasionally highly contaminated with radiation, in particular with caesium 137. For good detection of any contamination by radiation, in this case provision is made according to the invention for the optical element to be manufactured from a material which allows beta radiation to pass through.

Furthermore, provision is also made according to the invention that both the radiation sensor and the optical element may be embodied changeably or interchangeably. The optical element may in particular also be embodied such that it is compatible with known optical interchange systems, for example for camera lenses.

One advantageous implementation of the inventive concept provides that the upper part of the chopping board, with the exception of the optical element, is produced from a material which is impermeable to electromagnetic radiation, in particular to visible light. Due to such a configuration of the chopping board according to the invention, it is possible for the upper part to be able to be embodied corresponding to a user's aesthetic requirements. The upper part may be manufactured for example from solid wood, metal, plastics material or the like.

One advantageous configuration of the invention provides that an electromagnetic radiation source, in particular a light source, is assigned to the radiation sensor, wherein the radiation source is brought into an operative connection with the optical element such that the foodstuff to be chopped can be irradiated, in particular illuminated, by the radiation source, and wherein propagation of the radiation emitted by the radiation source can be adapted such that radiation reflected by the foodstuff to be chopped can be conducted to the radiation sensor by means of the optical element. Such a configuration of the chopping board according to the invention makes it possible for the foodstuff to be chopped to be able to be investigated by means of a method which is similar to reflected-light microscopy.

Furthermore, it is likewise possible and provided according to the invention that the emitted radiation may have a frequency spectrum which excites fluorescence of the foodstuff to be chopped, so that investigation of the foodstuff to be chopped can be carried out by means of a method which has analogies with fluorescence microscopy.

In one advantageous configuration of the chopping board according to the invention, provision is made that the base comprises force sensors, wherein the upper part is located on the force sensors by the fasteners, and wherein a weight force exerted by the upper part and by a foodstuff to be chopped arranged on the upper part is introduced fully into the force sensors. Provision is made according to the invention that the chopping board thus configured may also have a weighing function. It is advantageous in this case in particular that separate kitchen scales can be dispensed with and workflows in the kitchen can be simplified.

It is particularly advantageous in the case of the chopping board according to the invention that the removable upper part can be cleaned independently of the base which contains the measurement electronics. Thus provision is made in particular that the upper part can be configured such that it can be washed in a dishwasher, in particular also a domestic dishwasher. This increases the suitability of the chopping board for daily use and improves hygiene in the kitchen.

One advantageous implementation of the inventive concept provides that the base comprises at least one holding device for receiving a kitchen utensil. "Kitchen utensil" within the meaning of the inventive concept means in particular knives, mixers, bowls, measuring beakers or the like.

In one particularly advantageous implementation of the inventive concept, provision is made that the holding device is formed to receive a container, wherein the holding device is adapted to the container such that the container, when arranged as intended in the holding device, sits at least in portions with an edge formed protruding in its opening region on the holding device. In this case, provision is made for the holding device to be able to be adapted in particular to standardized kitchen containers, for example so-called "Gastronorm containers" according to DIN 66075. As a result of the holding device being arranged on the base, objects arranged on the holding device have no effect on the weighing function according to the invention of the chopping board.

One advantageous configuration of the invention provides that the chopping board has a data processing device, wherein the radiation sensor and/or the force sensors are connected/connectable in a signal-conducting manner to the data processing device, wherein signals generated by the sensors can be evaluated and sensor data can be generated by means of the data processing device. Such integration of the data processing device in the chopping board according to the invention means that the chopping board can be formed as a so-called "smart device".

In one particularly advantageous implementation of the inventive concept, provision is made that the data processing device is arranged in the base. This means that the upper part which comes into contact with the foodstuff to be chopped and is possibly contaminated can be cleaned independently of the base, which when the chopping board is used as intended has no contact with the foodstuff to be chopped. This is in particular advantageous since the data processing device does not have to be designed such that it withstands the environmental factors occurring during a cleaning operation. This has in particular a positive effect on the production costs of the chopping board according to the invention which are to be expected, since hardening electronic components in particular against water and steam is cost-intensive and complex.

In one advantageous configuration of the chopping board according to the invention, provision is made that a data evaluation rule is stored in the data processing device, on the basis of which rule evaluation data can be generated from the sensor data. Due to such a configuration of the chopping board according to the invention, it is made possible, for example in the case of perishable foodstuffs, for their temperature to be able to be determined from the infrared radiation thereof and for it to be able to be established using the evaluation rule whether or not they are still suitable for further processing, wherein the evaluation data in this case possibly comprise for example the values "Yes", "No" or "Not to be eaten raw!".

One advantageous implementation of the inventive concept provides that the data processing device has a data memory and/or can be brought into an operative connection with a data memory in which the sensor data and/or evaluation data can be stored. As a result, it is for example possible for a processing temperature for foodstuffs to be able to be logged over a particular period.

In this case it is also possible and provided for the data memory to be able to be embodied in particular sealed, so that manipulation of the stored data is prevented, in order thus to be able to demonstrate quality control for food hygiene purposes. In one particularly advantageous configuration of the invention, provision is made that the data memory can be embodied as a removable data memory, for example a memory card, in particular an SD card, or a USB stick.

One advantageous configuration of the invention provides that sensor data sets and/or evaluation data sets can be formed by the data processing device from the sensor data and/or evaluation data stored in the data memory, wherein the data sets formed can be stored in the data memory. In this case it is in particular possible and provided according to the invention that the sensor data and/or evaluation data can be linked with further data in the evaluation data sets formed, in particular with a timestamp, a user ID or the like.

In one advantageous configuration of the chopping board according to the invention, provision is made that the chopping board has a display device, wherein the display device can be brought/is brought into an operative connection with the data processing device, and wherein sensor data and/or evaluation data and/or sensor data sets and/or evaluation data sets can be visualized by means of the display device. In this case provision is made in particular that temperatures, foodstuff designations, temperature profiles, foodstuff qualities, handling tips or the like can be displayed by means of the display device.

In one particularly advantageous configuration of the chopping board according to the invention, provision is made that the display device is connected to a touch-sensitive input device, so that interaction between a user of the chopping board and the chopping board is made possible.

One advantageous implementation of the inventive concept provides that the chopping board has a data transmission device, wherein sensor data and/or evaluation data and/or sensor data sets and/or evaluation data sets can be transmitted by means of the data transmission device to an external device, in particular a smartphone. With such a configuration of the chopping board according to the invention, it is made possible for the data transmitted by means of the data transmission device to be able to be evaluated by the external device.

In one particularly advantageous configuration of the invention, provision is made that specialized software is executed on the external device, which software is adapted to the chopping board according to the invention and makes possible evaluation, display, storage or the like of the data acquired by the chopping board. In this case it is also possible and provided according to the invention that the transmission of the data does not have to take place exclusively by means of the data transmission device, but that it for example is also possible for the data memory of the chopping board according to the invention to be inserted into the external device and that the data can be transmitted thus.

In a further, particularly advantageous, embodiment of the invention, provision is made for, for example, diet plans to be drawn up, health tips to be established, nutrition behavior logged or the like to be carried out, on the basis of the data acquired by means of the chopping board according to the invention.

Below, some examples of embodiment of the inventive concept, which are illustrated in the drawings, will be discussed in greater detail.

DETAILED DESCRIPTION

Figure 1:
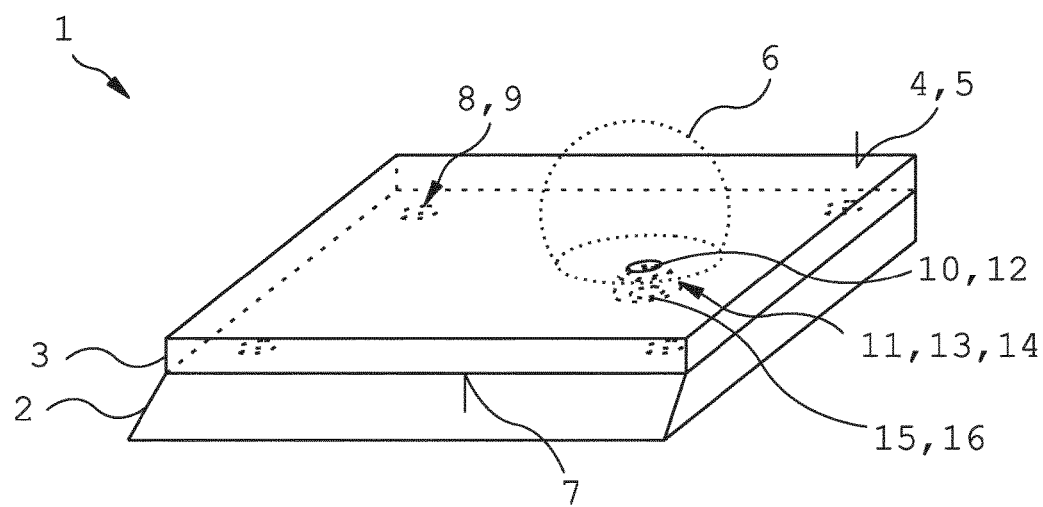
FIGS. 1, 2 and 4 show schematic representations of embodiments of the chopping board.

FIG. 1 shows a schematic representation of a chopping board 1 according to the invention for foodstuffs. The chopping board 1 illustrated has a base 2 and an upper part 3. The upper part 3 is placed on the base 2 and can be detached therefrom. A cutting surface 5 is formed on an upper-part upper side 4. In the embodiment of the chopping board 1 according to the invention illustrated, the complete upper-part upper side 4 is formed as a cutting surface 5. Foodstuff to be chopped 6 can be arranged and cut on the cutting surface 5.

The upper part 3 has fasteners 8 on an upper-part lower side 7 opposite the cutting surface and facing the base. The upper part 3 is located on the base 2 by means of these fasteners 8. In the embodiment of a chopping board 1 according to the invention illustrated, the fasteners 8 are located on force sensors 9 in recesses (not designated) formed on the base 2. A weight force exerted by the upper part 3 and the foodstuff to be chopped 6 is introduced fully into the force sensors 9.

The upper part 3 of the embodiment of the chopping board 1 according to the invention illustrated has an optical element 10. The optical element 10 comprises a circular sensor recess 11 which completely penetrates the upper part 3, and also a transparent disc 12 which is arranged in the sensor recess 11 and which closes off flush with the cutting surface 5. By means of the disc 12 and the sensor recess 11, visible light emitted by the foodstuff to be chopped 6 can be propagated through the upper part 3.

In a sensor area 13 of the base 2 which is assigned to the optical element 10, an interferometer 15 is arranged in a sensor receptacle 14 adapted to the sensor recess 11, by means of which interferometer the electromagnetic radiation can be detected, so that characteristics of the foodstuff to be chopped 6 can be determined.

The chopping board 1 also has a light source 16 which is arranged adjacent to the interferometer 15 in the sensor receptacle 14. By means of the light source 16, the foodstuff to be chopped 6 can be irradiated with visible light through the optical element 10.

Figure 2:
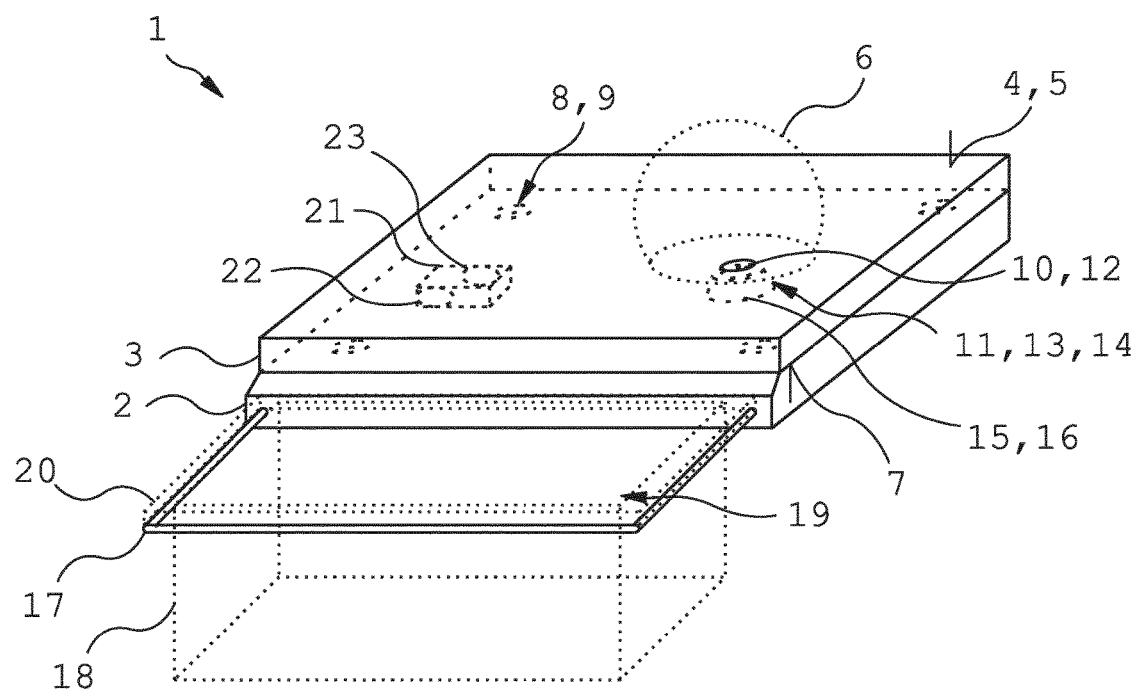

Unlike in the embodiment illustrated in FIG. 1, in the embodiment of the chopping board 1 illustrated in FIG. 2 the base 2 comprises a holding device 17 for receiving a container 18, wherein an exemplified container 18 is shown in FIG. 2. The holding device 17 is adapted to the container 18 such that the container 18 sits in portions with an edge 20 formed protruding in its opening region 19 on the holding device 17.

The embodiment of the chopping board 1 illustrated also has a data processing device 21 which is brought into an operative connection with the force sensors 9 and the interferometer 15. Furthermore, the data processing device 21 has a data memory 22 and a data transmission device 23.

Figure 3:
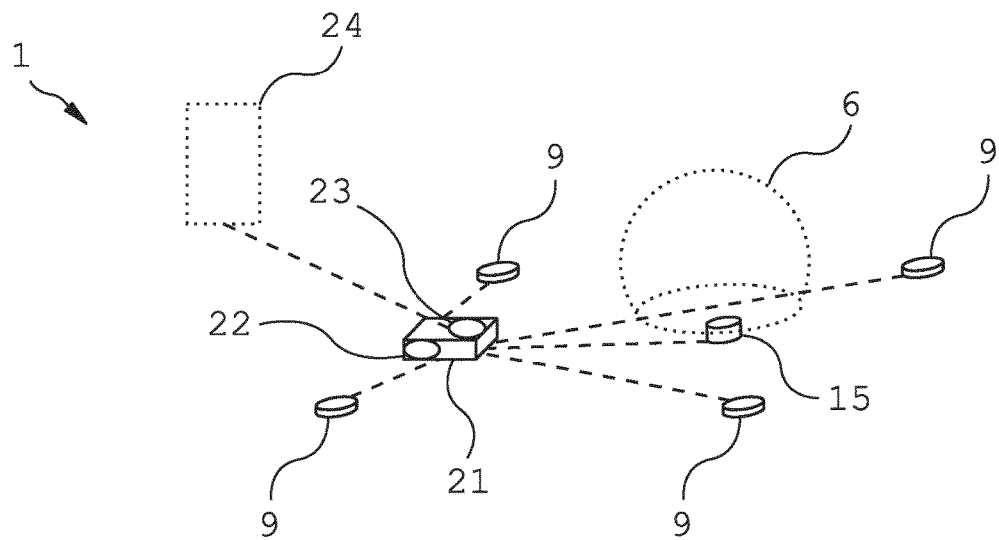
FIG. 3 shows a simplified schematic representation of the connections between electronic components of the chopping board.

It is illustrated schematically in FIG. 3 how in the embodiment of the chopping board 1 illustrated in FIG. 2 the data processing device 21 is connected in a signal-conducting manner to the interferometer 15 and the force sensors 9. By means of the data processing device 21, the signals generated by the sensors 9, 15 can be evaluated and sensor data generated. An evaluation rule is also stored in the data processing device 21, on the basis of which rule evaluation data can be generated from the sensor data. The sensor data and the evaluation data can be stored in the data memory 22.

FIG. 3 also shows an external device 24 to which data are transmitted by the data processing device 21 by means of the data transmission device 23. Information about the foodstuff to be chopped can be acquired from the data by means of the external device 24.

Figure 4:
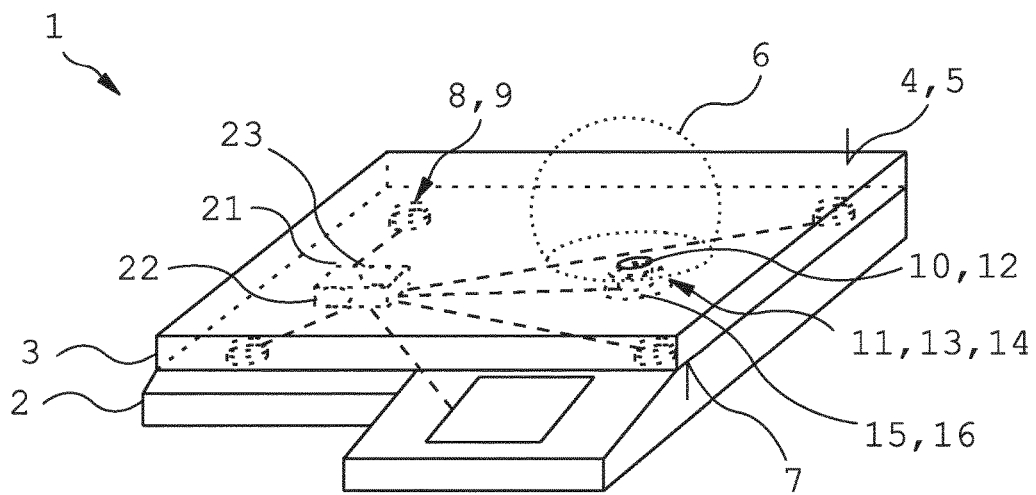

The embodiment of the chopping board 1 according to the invention illustrated in FIG. 4 has an integrated display device 25 which is connected in a signal-conducting manner to the data processing device 21. The evaluation data acquired by the data processing device 21 can be visualized by means of the display device 25.

LIST OF REFERENCE NUMERALS 1. chopping board
2. base
3. upper part
4. upper-part upper side
5. cutting surface
6. foodstuff to be chopped
7. upper-part lower side
8. fastener
9. force sensor
10. optical element
11. sensor recess
12. disc
13. sensor area
14. sensor receptacle
15. interferometer
16. light source
17. holding devices
18. container
19. opening region
20. edge
21. data processing device
22. data memory
23. data transmission device
24. external device
25. display device

The invention claimed is:

1. A chopping board (1) for foodstuffs, comprising:
a base (2) and
at least one upper part (3) which can be arranged detachably on the base (2),
wherein a cutting surface (5) on which foodstuff to be chopped (6) can be arranged and cut is formed on an upper-part upper side (4) facing away from the base (2) when the upper part (3) is arranged as intended on the base (2), wherein the upper part (3) comprises fasteners (8), by which the upper part (3) is located on the base (2), on an upper-part lower side (7) opposite the cutting surface (5) and facing the base (2), wherein the base (2) of the chopping board (1) comprises at least one bearing surface on a base lower side facing away from the upper part (3), by which bearing surface the chopping board (1) sits on a supporting surface, wherein the upper part (3) comprises at least one optical element (10), by which electromagnetic radiation emitted and/or reflected by the cut foodstuff can be propagated through the upper part (3), and wherein at least one radiation sensor for detecting electromagnetic radiation is arranged in a sensor area of the base (2) assigned to the optical element (10), by which sensor the electromagnetic radiation can be detected, so that characteristics of the foodstuff to be chopped (6) can be determined.

2. The chopping board (1) according to claim 1,
wherein the electromagnetic radiation is electromagnetic radiation in the near-infrared range, and
wherein the radiation sensor is an interferometer (15).

3. The chopping board (1) according to claim 1,
wherein the upper part (3) of the chopping board (1), with exception of the optical element (10), is produced from a material which is impermeable to visible light.

4. The chopping board (1) according to claim 1,
wherein an electromagnetic radiation source is assigned to the radiation sensor,
wherein the electromagnetic radiation source is brought into an operative connection with the optical element (10) such that the foodstuff to be chopped (6) can be irradiated by the electromagnetic radiation source, and
wherein propagation of the radiation emitted by the electromagnetic radiation source is adapted such that radiation reflected by the cut foodstuff is conducted to the radiation sensor by the optical element (10).

5. The chopping board (1) according to claim 4,
wherein the electromagnetic radiation source is a light source (16).

6. The chopping board (1) according to claim 1,
wherein the base (2) comprises force sensors (9),
wherein the upper part (3) is located on the force sensors (9) by the fasteners (8), and
wherein a weight force exerted by the upper part (3) and by the foodstuff to be chopped (6) arranged on the upper part (3) is introduced fully into the force sensors (9).

7. The chopping board (1) according to claim 1,
wherein the base (2) comprises at least one holding device (17) for receiving a kitchen utensil.

8. The chopping board (1) according to claim 1,
wherein the base (2) comprises at least one holding device (17) for receiving a container (18),
wherein the holding device is adapted to the container such that the container when arranged as intended in the holding device (17) sits at least in portions with an edge (20) formed protruding in its opening region (19) on the holding device (17).

9. The chopping board (1) according to claim 6,
wherein the chopping board (1) comprises a data processing device (21),
wherein the radiation sensor and/or the force sensors (9) are connected in a signal-conducting manner to the data processing device (21),
wherein signals generated by the radiation sensor and the force sensors are evaluated and sensor data is generated by the data processing device (21).

10. The chopping board (1) according to claim 9,
wherein an evaluation rule is stored in the data processing device (21), on the basis of which rule evaluation data is generated from the sensor data.

11. The chopping board (1) according to claim 10,
wherein the data processing device (21) comprises a data memory (22) in which the sensor data or the evaluation data is stored.

12. The chopping board (1) according to claim 11,
wherein sensor data sets or evaluation data sets are formed by the data processing device (21) from the sensor data or the evaluation data stored in the data memory (22),
wherein the data sets formed are stored in the data memory (22).

13. The chopping board (1) according to claim 12,
wherein the chopping board (1) comprises a display device (25),
wherein the display device (25) is brought into an operative connection with the data processing device (21), and
wherein the sensor data or the evaluation data or the sensor data sets or the evaluation data sets are visualized by the display device (25).

14. The chopping board (1) according to claim 12,
wherein the chopping board (1) comprises a data transmission device (23),
wherein the sensor data or the evaluation data or the sensor data sets or the evaluation data sets are transmitted by the data transmission device (23) to an external device (24).

15. The chopping board (1) according to claim 10,
wherein the data processing device (21) is brought into an operative connection with a data memory (22) in which the sensor data and/or the evaluation data is stored.

* * * * *